United States Patent [19]

Gesellchen et al.

[11] Patent Number: 4,510,082

[45] Date of Patent: Apr. 9, 1985

[54] PHARMACOLOGICALLY ACTIVE PEPTIDES

[75] Inventors: Paul D. Gesellchen, Indianapolis; Robert T. Shuman, Greenwood, both of Ind.

[73] Assignee: Eli Lilly and Company, Indianapolis, Ind.

[21] Appl. No.: 472,438

[22] Filed: Mar. 7, 1983

[51] Int. Cl.³ ............................................. C07C 103/52
[52] U.S. Cl. ........................ 260/112.5 R; 260/112.5 E
[58] Field of Search .................. 260/112.5 R, 112.5 E

[56] References Cited

U.S. PATENT DOCUMENTS 4,320,051  3/1982  Sarantakis .................. 260/112.5 E
4,322,340  3/1982  Shuman et al. ............. 260/112.5 E
4,333,873  6/1982  Shuman ...................... 260/112.5 E

OTHER PUBLICATIONS

Chang et al., *Life Sciences*, 18, 1473–1482 (1976).
Dutta et al., *Life Sciences*, 21, 559–562 (1977).
Belluzzi et al., *Life Sciences*, 23, 99–104 (1978).
Roemer et al., *Nature*, 268, 547–549 (1977).
Dutta et al., *Acta Pharm. Sciences*, 14, 14–16 (1977).
Roques et al., *Eur. J. Pharmacol.* 60, 109–110 (1979).
Kiso et al., *Eur. J. Pharmacol.* 71, 347–348 (1981).

*Primary Examiner*—Delbert R. Phillips
*Assistant Examiner*—F. T. Moezie

*Attorney, Agent, or Firm*—William C. Martens, Jr.; Arthur R. Whale

[57] ABSTRACT

Compounds of the formula

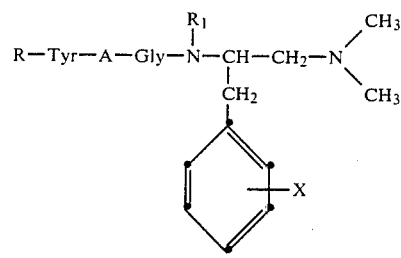

and pharmaceutically acceptable non-toxic acid addition salts thereof, in which R is hydrogen, methyl, ethyl, cyclopropylmethyl, or allyl;

A is a residue of a D-amino acid selected from the goup consisting of Ala, Abu, Nva, Val, Nle, Leu, Ile, Gly-(Al), Gly(Cp) Met, Cys(Me), Met(O), Cys(Me) (O), Ser, Ser(Me), Thr, and Hse;

$R_1$ is hydrogen, $C_1$–$C_3$ primary alkyl, cyclopropylmethyl, allyl, ethylthiomethyl, 2-fluoroethyl, or propargyl; and X is hydrogen, fluoro, bromo, iodo, chloro, hydroxy, $C_1$–$C_3$ alkyl, trifluoromethyl, or $C_1$–$C_2$ alkoxy; are useful analgesic agents.

18 Claims, No Drawings

PHARMACOLOGICALLY ACTIVE PEPTIDES

BACKGROUND OF THE INVENTION

This invention relates to a novel class of compounds which exhibit analgesic activity.

Recently, endogenous substances having morphine-like properties have been extracted from mammalian brain or csf. These substances, named enkephalin, have been identified by Hughes et al., Nature 258, 577 (1975) as pentapeptides having the following sequences:
H-Tyr-Gly-Gly-Phe-Met-OH
H-Tyr-Gly-Gly-Phe-Leu-OH.
These compounds are referred to as methionine-enkephalin and leucine-enkephalin, respectively.

Although methionine and leucine enkephalin have been shown to exhibit analgesic activity in mice upon administration intracerebroventricularly [Buscher et al., Nature, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., Life Sciences 21, pp. 559–562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., Nature 268, pp. 547–549 (1977), suggest modification of the Met[5] to its corresponding carbinol and oxidation of the Met sulfur to the sulfoxide as useful modifications.

Another structural modification of significance is that reported in U.S. Pat. No. 4,322,342. This publication suggests enhancement of activity and bioavailability of enkephalin analogs by insertion of a D-amino acid residue in position 2, conversion of the terminal carboxyl to an amide, and N-alkylation of the amino acid residue in position 5.

Roques et al., Eur. J. Pharmacol. 60, 109–110 (1979), describe, among others, Tyr-D-Ala-Gly-NH(phenethyl), Tyr-D-Ala-Gly-NH-CH(CH$_3$)CH$_2$CH(CH$_3$)$_2$, and Tyr-D-Met-Gly-NH-CH(CH$_3$)CH$_2$CH(CH$_3$)$_2$.

Kiso et al., Eur. J. Pharmacol. 71, 347–348 (1981), describe among others, Tyr-D-Met(O)-Gly-NH-(phenethyl) and Tyr-D-Met(O)-Gly-N(CH$_3$)(phenethyl).

U.S. Pat. No. 4,320,051 describes compounds which include, among others,

Tyr—D-(amino

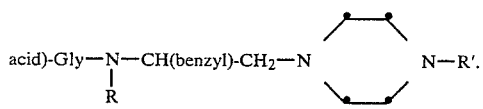

acid)-Gly—N—CH(benzyl)-CH$_2$—N    N—R'.
         |
         R

A new class of compounds has been discovered which exhibit analgesic activity and which have markedly low levels of physical dependence liability. These compounds are substituted tripeptides, the C-terminal portion of which contains a dimethylamino group.

SUMMARY OF THE INVENTION

Thus, this invention relates to a class of compounds having the formula

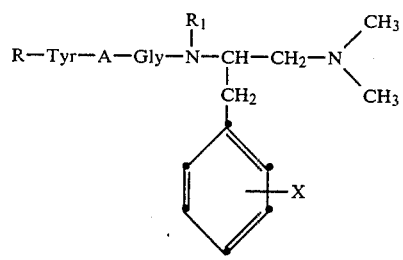

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me)(O), Ser, Ser(Me), Thr, and Hse;

R$_1$ is hydrogen, C$_1$–C$_3$ primary alkyl, cyclopropylmethyl, allyl, ethylthiomethyl, 2-fluoroethyl, or propargyl; and X is hydrogen, fluoro, bromo, iodo, chloro, hydroxy, C$_1$–C$_3$ alkyl, trifluoromethyl, or C$_1$–C$_2$ alkoxy.

DETAILED DESCRIPTION OF THE INVENTION

As indicated above, the compounds of this invention have the following structure:

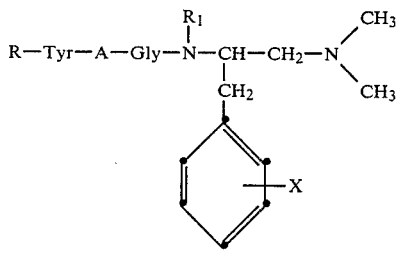

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which thereby are defined can be viewed as having arisen from tetrapeptides, the C-terminal portion of which is reduced and modified to a defined amine.

The stereoconfiguration of the compounds of this invention is an essential feature thereof. The amino acid residues of the compounds of this invention, which for the sake of convenience can be viewed as tetrapeptides, are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists.

The group $R_1$ as used herein is defined to include the group "$C_1$–$C_3$ primary alkyl". By the term "$C_1$–$C_3$ primary alkyl" is meant methyl, ethyl, and n-propyl.

The group X as used herein is defined to include the group "$C_1$–$C_3$ alkyl". By the term "$C_1$–$C_3$ alkyl" is intended methyl, ethyl, n-propyl and isopropyl.

The group X as used herein is defined to include the group "$C_1$–$C_2$ alkoxy". By the term "$C_1$–$C_2$ alkoxy" is meant methoxy and ethoxy.

With respect to the particular position residues of the tetrapeptides of this invention, the following considerations prevail:

(A) Position 1

This position represents the amino-terminal portion of the peptide. The residue is that which results from L-tyrosine. The residue can be N-unsubstituted, in which case R is hydrogen. Moreover, the residue can be N-mono-substituted, giving rise to N-methyl, N-ethyl-, N-cyclopropylmethyl-, or N-allyl-. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue preferably is N-substituted. In the event that the tyrosyl is N-substituted, the N-substituent preferably is methyl.

(B) Position 2

The amino acid residue (A) which is present in the second position of the peptides of this invention must be the D stereoisomer and is any of several α-amino acid residues depending upon the substituent ($R_4$) on the α-carbon. These include residues derived from D-alanine (Ala) ($R_4$ is methyl), D-α-aminobutyric acid (Abu) ($R_4$ is ethyl), D-norvaline (Nva) ($R_4$ is n-propyl), D-valine (Val) ($R_4$ is isopropyl), D-norleucine (Nle) ($R_4$ is n-butyl), D-leucine (Leu) ($R_4$ is isobutyl), D-isoleucine (Ile) ($R_4$ is sec-butyl), D-allylglycine [Gly(Al)] ($R_4$ is allyl), D-cyclopropylmethylglycine [Gly(Cp)] ($R_4$ is cyclopropylmethyl), D-methionine (Met) ($R_4$ is 2-methylthioethyl), D-(S-methyl)cysteine [Cys(Me)] ($R_4$ is methylthiomethyl), D-methionine sulfoxide [Met(O)] ($R_4$ is methylsulfinylethyl), D-(S-methyl)cysteine sulfoxide [Cys(Me)(O)] ($R_4$ is methylsulfinylmethyl), D-serine (Ser) ($R_4$ is hydroxymethyl), D-threonine (Thr) ($R_4$ is 1-hydroxyethyl), and D-homoserine (Hse) ($R_4$ is 2-hydroxyethyl). Preferably, A is Ala, Nva, Val, Nle, Leu, Ile, Ser, Met, Met(O), Thr, Hse, or Ser(Me), and, more preferably, is Ala, Met, Met(O), Nva, Ser(Me), or Nle. Most preferably, A is Ala.

(C) Position 3

The amino acid residue present in this position is that derived from glycine (Gly).

(D) Position 4

The moiety present in this position is not, strictly speaking, an amino acid residue. Instead, it is an amine.

The structure of the amine can be viewed as the reduction product of the N,N-dimethylamide of L-phenylalanine or of a ring-substituted L-phenylalanine. The moiety thereby defined and joined to the remainder of the molecule through —$NR_1$— thus is 1-benzyl-2-dimethylaminoethyl or a ring-substituted derivative thereof. If the ring is substituted, it preferably is mono-substituted in the meta or para position and, if substituted, preferably is fluoro, bromo, iodo, chloro, methyl, ethyl, n-propyl, isopropyl, trifluoromethyl, methoxy, or ethoxy. If substituted, the substituent most preferably is p-fluoro, m-bromo or m-methyl.

The joining amino moiety (—$NR_1$—) may be unsubstituted ($R_1$ is hydrogen) or substituted. If substituted, $R_1$ is methyl, ethyl, n-propyl, cyclopropylmethyl, allyl, ethylthiomethyl, 2-fluoroethyl, or propargyl. Preferably, $R_1$ is $C_1$–$C_3$ primary alkyl, allyl, cyclopropylmethyl, or propargyl. Most preferably, $R_1$ is ethyl, cyclopropylmethyl, allyl, or propargyl.

In this specification, the following abbreviations, most of which are well known and are commonly used in the art, are employed:

Abu—α-aminobutyric acid
Ala—alanine
Cys—cysteine
Cys(Me)—(S-methyl)cysteine
Cys(Me)(O)—(S-methyl)cysteine sulfoxide
Gly—glycine
Gly(Al)—allylglycine
Gly(Cp)—cyclopropylmethylglycine
Hse—homoserine
Ile—isoleucine
Leu—leucine
Met—methionine
Met(O)—methionine sulfoxide
Nle—norleucine
Nva—norvaline
Phe—phenylalanine
Phe—N—1 benzyl-2-dimethylaminoethylamine
Ser—serine
Ser(Me)—O-methylserine
Thr—threonine
Tyr—tyrosine
Val—valine
Ac—acetyl
AcOMe—acetoxymethyl
Al—allyl
Cp-cyclopropylmethyl
Me—methyl
Et—ethyl
Ip—isopropyl
Pr—n-propyl
OMe—methoxy
Etm—ethylthiomethyl
Fle—2-fluoroethyl
Ppg—propargyl
Bu—n-butyl
i-Bu—isobutyl
t-Bu—t-butyl
s-Bu—sec-butyl
Boc—t-butyloxycarbonyl
Bzl—benzyl
Cbz—benzyloxycarbonyl
DCC—N,N'-dicyclohexylcarbodiimide
HOBt—1-hydroxybenzotriazole
DMF—N,N-dimethylformamide
TFA—trifluoroacetic acid
THF—tetrahydrofuran DEAE—diethylaminoethyl
NMM—N-methylmorpholine
IBCF—isobutyl chloroformate
18-crown-6—1,4,7,10,13,16-hexaoxacyclooctadecane Examples of typical compounds of this invention are the following, any or all of which may be in the form of a pharmaceutically acceptable nontoxic acid addition salt. In each of the following, the designation (Phe—N) represents phenylalanine converted to the dimethylamino structure. The presence of any ring substitution is noted in parenthesis following the Phe designation.

H-L-Tyr-D-Ala-Gly-L-(N-Me)Phe-N;
H-L-Tyr-D-Ala-Gly-L-(N-Et)Phe-N;
H-L-Tyr-D-Abu-Gly-L-(N-Pr)Phe(m-Br)-N;
H-L-Tyr-D-Abu-Gly-L-(N-Et)Phe-N;
H-L-Tyr-D-Nva-Gly-L-(N-Ppg)Phe(p-Me)-N;
H-L-Tyr-D-Nva-Gly-L-(N-Et)Phe(m-OMe)-N;
H-L-Tyr-D-Val-Gly-L-(N-Et)Phe(p-F)-N;
H-L-Tyr-D-Val-Gly-L-(N-Pr)Phe(p-Cl)-N;
H-L-Tyr-D-Nle-Gly-L-Phe(m-I)-N;
H-L-Tyr-D-Nle-Gly-L-(N-Ppg)Phe-N;
H-L-Tyr-D-Leu-Gly-L-(N-Etm)Phe-N;
H-L-Tyr-D-Leu-Gly-L-Phe-N;
H-L-Tyr-D-Ile-Gly-L-(N-Al)Phe(m-Br)-N;
H-L-Tyr-D-Ile-Gly-L-(N-Cp)Phe(p-Et)-N;
H-L-Tyr-D-Ala-Gly-L-(N-Et)Phe(p-OH)-N;
H-L-Tyr-D-Ala-Gly-L-Phe(p-OEt)-N;
H-L-Tyr-D-Ala-Gly-L-(N-Fle)Phe(o-Cl)-N;
H-L-Tyr-D-Ala-Gly-L-(N-Etm)Phe(m-I)-N;
H-L-Tyr-D-Ala-Gly-L-(N-Fle)Phe(p-I)-N;
H-L-Tyr-D-Ala-Gly-L-Phe-N;
H-L-Tyr-D-Ala-Gly-L-Phe-N;
H-L-Tyr-D-Ala-Gly-L-(N-Al)Phe-N;
H-L-Tyr-D-Ala-Gly-L-(N-Ppg)Phe-N;
H-L-Tyr-D-Thr-Gly-L-(N-Cp)Phe-N;
H-L-Tyr-D-Val-Gly-L-(N-Et)Phe-N;
H-L-Tyr-D-Leu-Gly-L-(N-Et)Phe(m-Br)-N;
H-L-Tyr-D-Val-Gly-L-Phe(m-Br)-N;
H-L-Tyr-D-Leu-Gly-L-(N-Al)Phe(p-F)-N;
H-L-Tyr-D-Thr-Gly-L-Phe(p-CF$_3$)-N;
H-L-Tyr-D-Thr-Gly-L-(N-Et)Phe(p-OEt)-N;
H-L-Tyr-D-Thr-Gly-L-(N-Me)Phe(m-Br)-N;
H-L-Tyr-D-Thr-Gly-L-(N-Pr)Phe(p-Br)-N;
H-L-Tyr-D-Thr-Gly-L-(N-Al)Phe(m-Cl)-N;
H-L-Tyr-D-Gly(Al)-Gly-L-(N-Et)Phe(p-Et)-N;
H-L-Tyr-D-Gly(Cp)-Gly-L-(N-Me)Phe-N;
H-L-Tyr-D-Met-Gly-L-(N-Et)Phe-N;
H-L-Tyr-D-Cys(Me)-Gly-L-(N-Cp)Phe(o-Br)-N;
H-L-Tyr-D-Met(O)-Gly-L-(N-Pr)Phe-N;
H-L-Tyr-D-Cys(Me)(O)-Gly-L-Phe(m-Br)-N;
H-L-Tyr-D-Ser-Gly-L-Phe(m-I)-N;
H-L-Tyr-D-Ser-Gly-L-(N-Et)Phe(p-Cl)-N;
(N-Me)-L-Tyr-D-Ala-Gly-L-(N-Cp)Phe-N;
(N-Me)-L-Tyr-D-Thr-Gly-L-(N-Et)Phe(p-I)-N;
H-L-Tyr-D-Hse-Gly-L-(N-Cp)Phe-N;
(N-Me)-L-Tyr-D-Ala-Gly-L-Phe-N;
(N-Me)-L-Tyr-D-Ala-Gly-L-(N-Me)Phe(m-Br)-N;
(N-Me)-L-Tyr-D-Ala-Gly-L-(N-Pr)Phe-N;
(N-Et)-L-Tyr-D-Abu-Gly-L-(N-Cp)Phe(p-I)-N;
(N-Me)-L-Tyr-D-Val-Gly-L-Phe(p-Pr)-N;
(N-Pr)-L-Tyr-D-Leu-Gly-L-(N-Cp)Phe(p-CF$_3$)-N;
H-L-Tyr-D-Abu-Gly-L-(N-Al)Phe(m-OMe)-N;
H-L-Tyr-D-Nle-Gly-L-(N-Al)Phe(o-Br)-N;
H-L-Tyr-D-Ile-Gly-L-(N-Ppg)Phe(p-Br)-N;
(N-Me)-L-Tyr-D-Leu-Gly-L-(N-Et)Phe(m-Br)-N;
(N-Me)-L-Tyr-D-Nva-Gly-L-(N-Me)Phe(p-Ip)-N;
(N-Me)-L-Tyr-D-Ala-Gly-L-(N-Ppg)Phe(p-Pr)-N;
(N-Et)-L-Tyr-D-Ala-Gly-L-(N-Me)Phe-N;
(N-Cpm)-L-Tyr-D-Ala-Gly-L-(N-Me)Phe-N;
(N-Me)-L-Tyr-D-Ala-Gly-L-(N-Cp)Phe-N;
(N-Al)-L-Tyr-D-Ala-Gly-L-(N-Al)Phe-N;
(N-Me)-L-Tyr-D-Ala-Gly-L-(N-Etm)Phe-N;
(N-Et)-L-Tyr-D-Ala-Gly-L-(N-Et)Phe-N;
(N-Cpm)-L-Tyr-D-Ala-Gly-L-(N-Et)Phe(m-Me)-N;
(N-Me)-L-Tyr-D-Ala-Gly-L-(N-Al)Phe(p-OEt)-N;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by classical solution phase synthesis.

Preparation involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HOBt). The presence of HOBt suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A more complete discussion of the techniques which are available for selective cleavage is provided in the literature in Schröder and Lübke, *The Peptides,* Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of an unprotected tyrosyl residue.

A preferred specific method for preparing the compounds of this invention involves coupling a dipeptide representing the amino acid residues in the 2- and 3-positions with the C-terminal phenylalanine derivative following which the resulting peptide is coupled to the N-terminal tyrosine. The general sequence is depicted by the scheme provided hereinbelow. In the sequence, the letter Z represents the C-terminal moiety, and the symbol AA represents an amino acid residue.

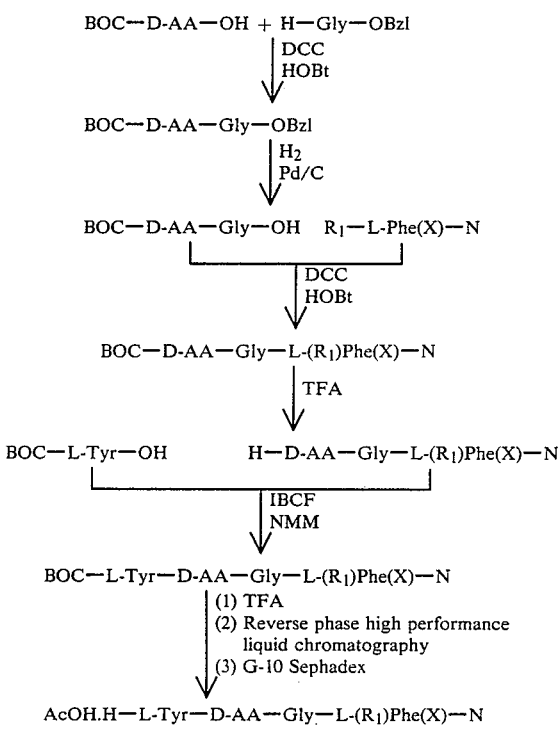

The above represents only one sequence for preparing compounds of this invention. Other sequences, of course, are available. One involves coupling a separately prepared N-terminal tripeptide with a separately prepared C-terminal phenylalanine derivative followed by appropriate deblocking of any remaining blocked moieties. Another solution method which can be employed involves the step-wise, sequential addition of single amino acids in construction of the peptide chain beginning with the C-terminal moiety. Reaction techniques such as those described above are employed in this as well as any other contemplated preparative sequence.

In certain of the compounds of this invention, one or more of the groups R and $R_1$ are, variously, alkyl, allyl, propargyl, ethylthiomethyl, 2-fluoroethyl, or cyclopropylmethyl. In these instances, the appropriate N-substituted amino acid is employed in the preparative sequence. Any of the N-monosubstituted amino acids can be prepared as follows using an N-protected amino acid as starting material:

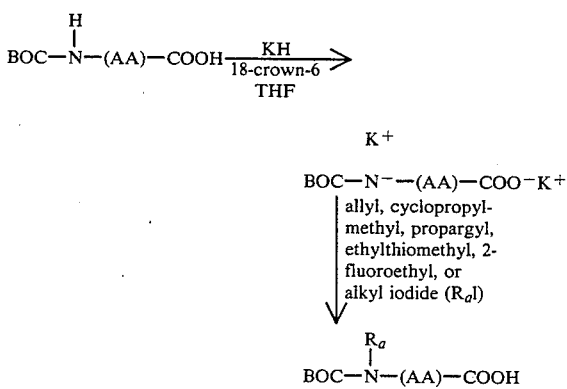

As the above sequence indicates, the amino acid first is treated with potassium hydride in the presence of a suitable crown ether to generate the dianion. The intermediate then is treated with the appropriate allyl, cyclopropylmethyl, propargyl, ethylthiomethyl, 2-fluoroethyl, or alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even if racemization occurs, the product can be purified by recrystallization as the salt of d(+)α-methylphenylethylamine.

The compounds of this invention are valuable pharmaceutical agents. They exhibit analgesic activity and are especially useful in alleviation of pain when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispensing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 0.5 μg. to about 2 mg. per kilogram body weight of the recipient, and, preferably, from about 10 μg. to about 100 μg, per kilogram body weight, when administered intramuscularly or subcutaneously, and from about 0.1 μg. to about 200 μg. per kilogram body weight of the recipient, and, preferably, from about 1 μg, to about 50 μg, per kilogram body weight, when administered intravenously. When administered orally, the dosage generally will range from about 100 μg. to about 100 mg. per kilogram body weight of the recipient, and, preferably, from about 500 μg. to about 50 mg. per kilogram body weight, and, more preferably, from about 1 mg. to about 10 mg. per kilogram body weight.

The following examples are provided to illustrate the preparation and activity of the compounds of this invention. They are not intended to be limiting upon the scope thereof.

EXAMPLE 1

Preparation of L-(N-Methyl)tyrosyl-D-alanylglycine, [N-ethyl-N-(1-benzyl-2-dimethylamino)ethyl]amide, Diacetate Salt.

A. $N^\alpha$-t-Butyloxycarbonyl-$N^\alpha$-ethyl-L-phenylalanine, N,N-dimethylamide.

$N^\alpha$-t-butyloxycarbonyl-$N^\alpha$-ethyl-L-phenylalanine, dicyclohexylamine salt (19.0 g., 40 mmol.) was dissolved in 100 ml. of DMF. The mixture was cooled to 0° C., and 3.3 g. (40 mmol.) of dimethylamine hydrochloride were added. The mixture then was magnetically stirred at 0° C. for 15 minutes. HOBt (5.4 grams; 40 mmol.) and DCC (8.3 grams; 40 mmol.) were added. The mixture was stirred for 2 hours at 0° C. and then for 24 hours at room temperature, after which it was cooled to 0° C. and filtered. The filtrate was concentrated in vacuo to an oil. The oil was dissolved in ethyl acetate, and the solution was extracted successively with 1N sodium bicarbonate, water, cold 1.5N citric acid, and water. The organic phase was dried over magnesium sulfate and concentrated in vacuo to give 13.4 g. (104% of theory) of the title compound as a solid.

NMR δ (Boc), 1.3; δ[—N(CH$_3$)$_2$], 2.9.

Mass Spec.—320 (parent ion).

B. 1-Ethylamino-1-benzyl-2-dimethylaminoethane

To a round bottom flask containing 30 ml. of dry pyridine were added 1.1 grams (30 mmol.) of sodium borohydride and 3.2 grams (10 mmol.) of the product from part A. The mixture was stirred at reflux for 40 hours, after which it was cooled to room temperature and concentrated in vacuo to an oil. Aqueous citric acid (1.5$\underline{N}$) was slowly added to the mixture over a one hour period. The resulting solution was adjusted to pH 5.0 by addition of 1$\underline{N}$ HCL. The aqueous solution then was extracted once with ethyl acetate, and the pH then was adjusted to 9.5 with 2$\underline{N}$ NaOH. The aqueous solution then was extracted with ethyl acetate, dried over magnesium sulfate, and evaporated in vacuo to give 1.2 grams (58%) of the title compound as an oil.

NMR δ (phenyl), 7.2; δ [—N(CH$_3$)$_2$], 2.2.

$[α]_D^{25}$ +28.78° (c=0.5 in MeOH).

C. N$^α$-t-Butyloxycarbonyl-D-alanylglycine, [N-ethyl-N-(1-benzyl-2-dimethylamino)ethyl]amide.

To 15 ml. of DMF were added 824 mg. (4 mmol.) of the product from part B. The mixture was cooled to 0° C., and 1.06 grams (4 mmol.) of N$^α$-t-butyloxycarbonyl-D-alanylglycine, 540 mg. (4 mmol.) of HOBt, and 824 mg. (4 mmol.) of DCC were added. The mixture was stirred at 0° C. for 4 hours and then at room temperature for 72 hours. The mixture was cooled to 0° C., solids were removed by filtration, and the filtrate was evaporated in vacuo. The residue was dissolved in a mixture of ethyl acetate and water, and the pH was adjusted to 9.5 with 2$\underline{N}$ NaOH. The ethyl acetate layer was separated, extracted once with water, dried over magnesium sulfate, and evaporated in vacuo to oil. The oil was applied to a Water's silica column and run with a step gradient of acetonitrile→tetrahydrofuran on a Water's Preparative LC/System 500A. The product was isolated according to the thin-layer profile of the fractions collected to give 1.7 grams (100%) of the title compound.

$[α]_D^{25}$ +7.60° (c=0.3 in MeOH).

Analysis, calculated for C$_{23}$H$_{38}$N$_4$O$_4$ (434.6): C, 63.57; H, 8.81; N, 12.89. Found: C, 63.87; H, 8.71; N, 12.49.

D. N$^α$-t-Butyloxycarbonyl-L-(N-methyl)tyrosyl-D-alanylglycine, [N-ethyl-N-(1-benzyl-2-dimethylamino)ethyl]amide.

To 20 ml. of trifluoroacetic acid containing 3 ml. of anisole were added 1.7 grams (3.9 mmol.) of the product from part C. The mixture was stirred at 0° C. for 30 minutes after which the solvent was evaporated in vacuo without addition of heat. The resulting oil was treated several times by addition and decanting of ethyl ether. The remaining oil then was dissolved in a mixture of ethyl acetate and water, and the pH was adjusted to 10.0 by addition of 2$\underline{N}$ NaOH. The organic phase then was separated, dried over magnesium sulfate, and concentrated in vacuo to an oil.

N$^α$-t-Butyloxycarbonyl-N$^α$-methyl-L-tyrosine, dicyclohexylamine salt (1.86 grams; 3.9 mmol.) was dissolved in 15 ml. of DMF, and the solution was cooled to −15° C. NMM (3 drops) and IBCF (0.51 ml.; 3.9 mmol.) were added to the rapidly stirred solution. The solution was stirred at −15° C. while the free base of the above-prepared substituted dipeptide was dissolved in 5 ml. DMF and was cooled to 0° C. The cooled mixture then was added to the cooled, stirring solution of the mixed anhydride. The resulting mixture was stirred for 4 hours at −15° C. Solids were removed by filtration, and the filtrate was evaporated in vacuo. The resulting residue was dissolved in a mixture of ethyl acetate and water, and the pH was adjusted to 9.8 with 2$\underline{N}$ NaOH. The ethyl acetate was separated, dried over magnesium sulfate, and concentrated in vacuo to give 1.8 grams (76%) of the title compound as an oil.

NMR δ (Boc), 1.2; δ [—N(CH$_3$)$_2$], 2.2.

E. L-(N-Methyl)tyrosyl-D-alanylglycine, [N-ethyl-N-(1-benzyl-2-dimethylamino)ethyl]amide, diacetate salt.

The product from part D (1.7 grams) was dissolved in 25 ml. of trifluoroacetic acid containing 3 ml. of anisole. The mixture was stirred at 0° C. for 30 minutes and then was lyophilized to a solid. The resulting solid was dissolved in sufficient buffer (13% CH$_3$CN, 0.1$\underline{M}$ NH$_4$OAc at pH 4.1) to make 9.0 ml. The solution was applied to a 4×70 cm. column of C$_{18}$ silica gel which had been equilibrated with the same buffer. The eluate was monitored at 280 nm, and the appropriate fractions were combined and lyophilized to give a white solid. The material was dissolved in 8 ml. of 50% acetic acid and applied to a 2.5×90 cm. column of G-10 Sephadex. The column was eluted with 50% acetic acid, and the eluate was monitored at 280 nm. The appropriate fractions were combined and lyophilized to give 743 mg. (42%) of the title compound as a white solid.

$[α]_D^{25}$ +35.58° (c=0.5 in 1$\underline{M}$ HOAc).

Analysis, calculated for C$_{32}$H$_{49}$N$_5$O$_8$ (631.8): C, 60.84; H, 7.82; N, 11.09. Found: C, 61.15; H, 7.22; N, 11.32.

Amino acid analysis: Gly, 0.74; Ala, 1.09.

EXAMPLE 2

Preparation of L-(N-Methyl)tyrosyl-D-alanylglycine[N-ethyl-N-[1-(4'-fluorobenzyl)-2-dimethylamino]ethyl]amide, Diacetate Salt.

Using the method described in Example 1, the foregoing was prepared and exhibited the following properties:

$[α]_D^{25}$ +61.75° C. (c=0.5, 1$\underline{M}$ acetic acid).

Analysis, calculated for C$_{32}$H$_{48}$N$_5$O$_8$ (649.8): C, 59.15; H, 7.45; N, 10.78. Found: C, 58.86; H, 7.17; N, 10.62.

Amino acid analysis: Gly, 0.68; Ala, 1.00; NH$_3$, trace.

Field Desorption Mass Spectrometry: 530.

EXAMPLE 3

Preparation of L-(N-Methyl)tyrosyl-D-(O-methyl)-serylglycine, [N-ethyl-N-(1-benzyl-2-dimethylamino)ethyl]amide, Diacetate Salt.

A. N$^α$-t-Butyloxycarbonylglycine, [N-ethyl-N-(1-benzyl-2-dimethylamino)ethyl]amide.

To 40 ml. of DMF were added 5.3 grams (26 mmol.) of the product produced as in part B of Example 1. To the mixture then were added 4.5 grams (26 mmol.) of N$^α$-t-butyloxycarbonyl-glycine, 4.5 ml. (26 mmol.) of diisopropylethylamine, and 11.59 grams (26 mmol.) of benzotriazolyl-N. oxy trisdimethylaminophosphonium hexafluorophosphate (Sempa-Chimie). The mixture was stirred at room temperature for 48 hours after which it was concentrated in vacuo to an oil. The resulting residue was dissolved in a mixture of ethyl acetate and 1$\underline{N}$ aqueous sodium bicarbonate. The pH was adjusted to 10.0 with 5$\underline{N}$ NaOH. The ethyl acetate layer was separated, dried over magnesium sulfate, and evaporated in vacuo to an oil. The oil was dissolved in ethyl acetate, applied to a Water's silica gel column, and run with a step gradient of ethyl acetate→THF on a Water's Preparative LC/System 500A. The product was isolated according to the thin-layer profile of the fractions collected to give 7.3 grams (77%) of the title compound.

NMR δ (phenyl), 7.3; δ (Boc), 1.5; δ [—N(CH$_3$)$_2$], 2.5.

B. N$^α$-t-Butyloxycarbonyl-D-(O-methyl)serylglycine, [N-ethyl-N-(1-benzyl-2-dimethylamino)ethyl]amide.

To 25 ml. of trifluoroacetic acid containing 5 ml. of anisole were added 7.3 grams (20 mmol.) of the product from part A. The mixture was stirred at 0° C. for 30 minutes after which the solvent was evaporated in vacuo without addition of heat. The resulting oil was repeatedly diluted with ethyl ether, and the ethyl ether was decanted. The remaining ol then was dissolved in a mixture of ethyl acetate and water, and pH was adjusted to 10.0 with 2N NaOH. The organic phase was separated, dried over magnesium sulfate, and concentrated in vacuo to give 4.7 grams (89%) of an oil.

N$^α$-t-Butyloxycarbonyl-D-(O-methyl)serine, cyclohexylamine salt (1.7 grams; 5.35 mmol.) (prepared by the procedure of Jaeger, M., Ishric, S., and Wickerhauser, M., *Croat. Chem. Acta*, 28, 5 (1956)) was neutralized with a cold mixture of 2N HCl and ethyl acetate. The ethyl acetate layer was separated, dried over magnesium sulfate, and evaporated in vacuo. The resulting N$^α$-t-butyloxycarbonyl-D-(O-methyl)serine was dissolved in 20 ml. of DMF, and the solution was cooled to −15° C. NMM (0.55 ml.; 5 mmol.) and IBCF (0.66 ml.; 5 mmol.) were added rapidly to the stirring solution. The resulting mixture was stirred at −15° C. while the free base of the peptide prepared as above described was dissolved in 5 ml. of DMF, and the mixture was cooled to 0° C. This solution then was added to the above-prepared mixed anhydride, and the resulting mixture was stirred for 3 hours at −15° C. and then for 24 hours at room temperature. The mixture then was concentrated in vacuo to an oil. The resulting residue was dissolved in a mixture of ethyl acetate and water, and the pH was adjusted to 10.0 with 2N NaOH. The organic layer was separated, dried over magnesium sulfate, and concentrated in vacuo to afford 2.2 g. of the residue. This material then was dissolved n ethyl acetate and applied to a Water's silica gel column. The column was eluted with a step gradient of ethyl acetate→1:1 mixture of ethyl acetate and THF on a Water's Preparative LC/System 500A. The product was isolated according to the thin-layer profile of the fractions collected to give 2.0 g. (92%) of the title compound.

[α]$_D^{25}$ +2.79° (c=0.5, MeOH).

C. L-(N-Methyl)tyrosyl-D-(O-methyl)serylglycine, [N-ethyl-N-(1-benzyl-2-dimethylamino)ethyl]amide, diacetate salt.

To 20 ml. of trifluoroacetic acid containing 3 ml. of anisole were added 2.0 g. (4.3 mmol.) of the product from part B. The mixture was stirred at 0° C. for 30 minutes after which the product was precipitated by addition of 400 ml. of ethyl ether. The ether was decanted, and the resulting oil was treated several times by addition and decanting of ethyl ether. The remaining oil then was dissolved in a mixture of ethyl acetate and water, and the pH was adjusted to 10.0 with 2N NaOH. The organic phase was separated, dried over magnesium sulfate, and concentrated in vacuo to an oil.

To 15 ml. DMF were added 1.31 g. (2.75 mmol.) of N$^α$-t-butyloxycarbonyl-N$^α$-methyl-L-tyrosine, dicyclohexylamine salt. The solution was cooled to −15° C., and 3 drops of NMM and 0.36 ml. (2.75 mmol.) of IBCF were added rapidly to the stirring solution. The stirring was continued at −15° C. while the free base of the dipeptide produced as described above was dissolved in 5 ml. of DMF, and the mixture was cooled to −15° C. The resulting solution then was added to the previously prepared mixed anhydride, and the mixture was stirred at −15° C. for 4 hours and then at room temperature for 24 hours. The resulting solids were removed by filtration, and the filtrate was evaporated in vacuo. The resulting residue was dissolved in a mixture of ethyl acetate and water, and the pH was adjusted to 10.0 with 2N NaOH. The organic layer was separated, dried over magnesium sulfate, and concentrated in vacuo to obtain 1.9 g. (107% of theoretical) of an oil. The oil was dissolved in 20 ml. of trifluoroacetic acid containing 3 ml. of anisole, and the resulting mixture was stirred at 0° C. for 30 minutes. The mixture then was concentrated in vacuo to an oil. Ethyl ether was added to the oil, and a solid formed which was filtered and dried. The solid then was dissolved in sufficient buffer (18% CH$_3$CN, 0.1M NH$_4$OAc at pH 4.2) to make 9.0 ml. The solution was applied to a 4×70 cm. column of C$_{18}$ silica gel previously equilibrated with the same buffer. The eluate was monitored at 280 nm, and the appropriate fractions were combined and lyophilized to give a white solid. The white solid was dissolved in 6 ml. of 50% acetic acid, and the solution was applied to a 2.5×90 cm. column of G-10 Sephadex. The column was eluted with 50% acetic acid, and the eluate was monitored at 280 nm. The appropriate fractions were combined and lyophilized to give b 1.35 g. (74% of the title compound as a white solid.

[α]$_D^{25}$ +36.0 (c=0.5, 1M acetic acid).

Analysis, calculated for C$_{33}$H$_{51}$N$_5$O$_9$ (661.8): C, 59.89; H, 7.77; N, 10.58. Found: C, 59.71; H, 7.71; N, 10.57.

Amino acid analysis (μmol/mg): (1) 21 hour hydrolysis: Ser(Me), 0.251; Ser, 0.814*; Gly, 0.489. (2) 72 hour hydrolysis: Ser(Me), 0.031; Ser, 0.822*; Gly, 0.946.

*Ser(Me) is converted in part to Ser during the acid hydrolysis procedure.

P Field Desorption Mass Spectrometry: 542.

EXAMPLE 4

Preparation of L-(N-Methyl)tyrosyl-D-alanylglycine, [N-methyl-N-(1-benzyl-2-dimethylamino)ethyl]amide, Diacetate Salt.

A. N$^α$-t-Butyloxycarbonyl-N$^α$-methyl-L-phenylalanine, dimethylamide.

To 150 ml. of DMF were added 9.21 g. (0.02 mole) of N$^α$-t-butyloxycarbonyl-N$^α$-methyl-L-phenylalanine, dicyclohexylamine salt. The mixture was cooled to 0° C., and 1.63 g. (0.02 mole) of dimethylamine hydrochloride were added. The mixture was stirred at 0° C. for 2 minutes, and 2.7 g. (0.02 mole) of HOBt and 4.13 g. (0.02 mole) of DCC were added. The mixture was stirred for 7 hours at 0° C. and then for 19 hours at room temperature after which it was cooled to 0° C. and filtered. The filtrate was concentrated in vacuo to an oil, and the oil was dissolved in ethyl acetate. The ethyl acetate solution was extracted successively with 1N sodium bicarbonate, water, cold 1.5N citric acid, and water. The organic phase was dried over magnesium sulfate and concentrated in vacuo to give 6.08 g. (99%) of the title compound as a white solid.

NMR δ (phenyl), 7.2; δ (CH$_3$), 2.8; δ [—N(CH$_3$)$_2$], 2.9.

Analysis, calculated for C$_{17}$H$_{26}$N$_2$O$_3$ (306.4): C, 66.64; H, 8.55; N, 9.14. Found: C, 66.38; H, 8.28; N, 8.88.

Field Desorption Mass Spectrometry: 307.

B. 1-(N-t-Butyloxycarbonyl)methylamino-1-benzyl-2-dimethylaminoethane.

To 40 ml. of dry pyridine containing 2.16 g. (0.057 mole) of sodium borohydride were added 5.86 g. (0.019 mole) of the product from part A. The mixture was stirred at reflux for 48 hours after which it was cooled to room temperature and concentrated in vacuo to an oil. Hydrochloric acid (6$\underline{N}$) was slowly added to the residue over a one hour period. The resulting solution was adjusted to pH 5.0 by addition of 1$\underline{N}$ HCl and then was extracted with ethyl ether. The aqueous layer was separated, the pH was adjusted to 10.0 with 2E,uns/$\underline{N}$/NaOH, and the mixture was extracted with ethyl acetate. The ethyl acetate layer was dried over magnesium sulfate and evaporated in vacuo to an oil. The oil was dissolved in chloroform, and the solution was applied to a Water's silica column and chromatographed on a Water's Preparative LC/System 500A. The column was eluted with a step gradient of chloroform→THF. The product was isolated according to thin-layer profile of the fractions collected to give 2.5 g. (45%) of the title compound.

NMR $\delta$ (phenyl), 7.2; $\delta$ (Boc), 1.4; $\delta$ [—N(CH$_3$)$_2$], 2.2.

C. N$^\alpha$-t-Butyloxycarbonyl-N$^\alpha$-methyl-L-tyrosyl-D-alanylglycine, [N-methyl-N-(1-benzyl-2-dimethyamino)ethyl]amide.

To 30 ml. of glacial acetic acid containing 1$\underline{N}$ gaseous HCl and 2 ml. of anisole were added 2.2 g. (0.008 mole) of the product from part B. The mixture was stirred at room temperature for 30 minutes after which the product was precipitated by addition of ethyl ether. The supernate was decanted, and the residual oil was treated several times with ethyl ether which was then decanted. The resulting remaining oil then was dissolved in a mixture of ethyl acetate and water, and the pH was adjusted to 10.0 with 2$\underline{N}$ NaOH. The organic phase was separated, dried over magnesium sulfate, and concentrated in vacuo to an oil. The oil was dissolved in 30 ml. of DMF, and the solution was cooled to 0° C. To the mixture then were added 2.13 g. (0.005 mole) of N$^\alpha$-t-butyloxycarbonyl-N$^\alpha$-methyl-L-tyrosyl-D-alanyl-glycine, 0.68 g. (0.005 mole) of HOBt, and 1.03 g. (0.005 mole) of DCC. The mixture was stirred at 0° C. for 4 hours and then at room temperature for 19 hours. The mixture then was cooled to 0° C., the resulting precipitate was removed by filtration, and the filtrate was evaporated in vacuo. The residue was dissolved in a mixture of ethyl acetate and water, and the pH was adjusted to 10.0 with 2$\underline{N}$ NaOH. The organic layer was separated, dried over magnesium sulfate, and concentrated in vacuo to give 2.86 g. (95%) of the title compound as an oil.

E. L-(N-methyl)tyrosyl-D-alanylglycine, [N-methyl-N-(1-benzyl-2-dimethylamino)ethyl]amide, diacetate salt.

To 20 ml. of trifluoroacetic acid containing 2 ml. of anisole were added 2.8 g. (4.7 mmol.) of the product from part C. The resulting mixture was stirred at 0° C. for 30 minutes after which it was concentrated in vacuo without addition of heat. Ethyl ether was added to the resultant oil, and the solid which formed was collected by filtration. The resulting solid was dissolved in sufficient buffer (9% CH$_3$CH, 0.1$\underline{M}$ NH$_4$OAc at pH 4.2) to make 9.0 ml. The resulting solution was applied to a 4×70 cm. column of C$_{18}$ silica gel previously equilibrated with the same buffer. The column was eluted with the buffer, and the eluate was monitored at 280 nm. Appropriate fractions were combined and lyophilized to give a white solid. The solid was dissolved in 5 ml. of 0.2$\underline{M}$ acetic acid, and the solution was applied to a 2.5×90 cm. column of G-10 Sephadex. The column was eluted with 0.2$\underline{M}$ acetic acid, and the eluate was monitored 280 nm. The appropriate fractions were combined and lyophilized to give 411 mg. (14%) of the title compound as a white solid.

$[\alpha]_D^{25}$ +64.8 (c=0.5, 1$\underline{M}$ acetic acid).

Analysis, calculated for C$_{31}$H$_{47}$N$_5$O$_8$ (617.7): C, 60.27; H, 7.67; N, 11.34. Found: C, 60.12; H, 7.67; N, 11.60.

Amino acid analysis: Ala, 1.05; Gly, 0.95.

Field Desorption Mass Spectrometry: 498.

BIOLOGICAL ACTIVITY

The analgesic activity of the compounds of this invention is demonstrated by the mouse hot plate and mouse writhing tests. In the mouse hot plate test, an upright acrylic cylinder comprising, as its base, a hot plate surface which is maintained at 55° C. is used. A mouse (Harlan ND4) is given, by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table records ED$_{50}$ results obtained from this test. By the term "ED$_{50}$" is meant that dose which produces analgesia in 50% of the mice tested. Analgesia is defined as a response latency in the presence of test compound that is equal to or greater than the control response latency plus two standard deviations. The percent analgesia data are converted to probits, and the ED$_{50}$ is calculated by regression analysis of the dose-response data. Each dose response curve must have at least four points, and each point is determined using data from a minimum of ten treated mice and ten control mice.

In the mouse writhing test, a writhing response is defined as a contraction of the abdominal musculature followed by extension of the hind limbs. Acetic acid administered intraperitoneally (10 ml./kg.) at a concentration of 0.6% was used to induce a writhing response. Five Cox Standard albino mice weighing 20–22 g. after being fasted overnight were observed simultaneously for the writhing response. Each mouse was used only once. The observation period was then minutes and started five minutes following administration of the acetic acid. Inhibition of mouse writhing was calculated from the total number of writhes in the control and test compound-treated groups according to the following formula:

$$\text{Percent inhibition} = 100 - \frac{\text{experimental group} \times 100}{\text{control group}}$$

On the average, control mice exhibited 225–250 writhes during the ten minute observation period. The dose required to reduce the frequency of writhing by 50% is defined as the ED$_{50}$ and is calculated by "The use of Regression Line in Reverse", [Brownlee, K.A., *Statistical Theory and Methodology in Science and Engi-*

*neering,* 2nd Ed., New York, John Wiley and Sons (1965)].

The Table following provides results for compounds of this invention when tested in the mouse hot plate and mouse writhing tests.

TABLE $$CH_3-L\text{-}Tyr-D\text{-}(A)-Gly-L\text{-}N\underset{CH_2}{\overset{R_1}{|}}-CH-CH_2-N\underset{CH_3}{\overset{CH_3}{\diagup}}$$

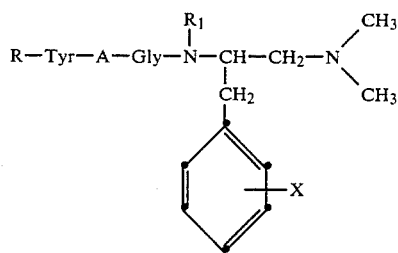

| Compound | | | Mouse Jump ED$_{50}$ | Mouse Writhing, ED$_{50}$, mg./kg. | |
|---|---|---|---|---|---|
| A | R$_1$ | X | mg./kg. | Subcutaneous | Oral |
| Ala | Et | H | 0.04 | 1.14 | 50.4 |
| Ala | Et | p-F | 0.04 | 2.1 | 88.2 |
| Ser(Me) | Et | H | 0.09 | 3.6 | 53.5 |
| Ala | Me | H | 0.05 | 1.81 | ~160 |

We claim:

1. A compound of the formula $$R-Tyr-A-Gly-N\underset{CH_2}{\overset{R_1}{|}}-CH-CH_2-N\underset{CH_3}{\overset{CH_3}{\diagup}}$$

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me) (O), Ser Ser(Me), Thr, and Hse;

R$_1$ is hydrogen, C$_1$-C$_3$ primary alkyl, cyclopropylmethyl, allyl, ethylthiometryl, 2-fluoroethyl, or propargyl; and X is hydrogen fluoro, bromo, iodo, chloro, hydroxy, C$_1$-C$_3$ alkyl, trifluoromethyl, or C$_1$-C$_2$ alkoxy.

2. Compound of claim 1, in which R is hydrogen.
3. Compound of claim 2, in which X is hydrogen.
4. Compound of claim 3, in which A is Ala, Nva, Val, Nle, Leu, Ile, Met, Met(O), Ser, Ser(Me), Thr, or Hse.
5. Compound of claim 4, in which A is Ala, Met, Met(O), Ser(Me), Nva, or Nle.
6. Compound of claim 5, in which A is Ala.
7. Compound of claim 6, in which R$_1$ is C$_1$-C$_3$ primary alkyl, cyclopropylmethyl, allyl, or propargyl.
8. Compound of claim 7, in which R$_1$ is ethyl, cyclopropylmethyl, allyl, or propargyl.
9. Compound of claim 8, in which R$_1$ is ethyl.
10. Compound of claim 9, in which R is hydrogen.
11. Compound of claim 9, in which R is methyl.
12. Compound of claim 6, in which R$_1$ is hydrogen.
13. Compound of claim 12, in which R is hydrogen.
14. Compound of claim 12, in which R is methyl.
15. Compound of claim 1, which is L-(N-methyl)-tyrosyl-D-alanylglycine, [N-ethyl-N-(1-benzyl-2-dimethylamino)ethyl]amide or a pharmaceutically acceptable non-toxic acid addition salt thereof.
16. Compound of claim 1, which is L-(N-methyl)-tyrosyl-D-alanylglycine, [N-ethyl-N-[1-(4'-fluorobenzyl)-2-dimethylamino]ethyl]amide or a pharmaceutically acceptable non-toxic acid addition salt thereof.
17. Compound of claim 1, which is L-(N-methyl)-tyrosyl-D-(O-methyl)serylglycine, [N-ethyl-N-(1-benzyl-2-dimethylamino)ethyl]amide or a pharmaceutically acceptable non-toxic acid addition salt thereof.
18. Compound of claim 1, which is L-(N-methyl)-tyrosyl-D-alanylglycine, [N-methyl-N-(1-benzyl-2-dimethylamino)ethyl]amide or a pharmaceutically acceptable non-toxic acid addition salt thereof.

* * * * *